United States Patent [19]

Grandi et al.

[11] Patent Number: 5,268,277
[45] Date of Patent: Dec. 7, 1993

[54] METHOD FOR THE PREPARATION OF HUMAN GROWTH HORMONE

[75] Inventors: Guido Grandi; Elisabetta Franchi; Federico Maisano; Silvia A. Testori, all of Milan, Italy

[73] Assignee: Eniricerche S.p.A., Milan, Italy

[21] Appl. No.: 834,486

[22] Filed: Feb. 12, 1992

Related U.S. Application Data

[63] Continuation of Ser. No. 223,162, Jul. 22, 1988, abandoned.

[30] Foreign Application Priority Data

Aug. 7, 1987 [IT] Italy .................. 21616 A 87

[51] Int. Cl.$^5$ .............. C12P 21/02; C12N 15/75; C12N 15/00
[52] U.S. Cl. ............... 435/69.4; 435/252.31; 435/320.1
[58] Field of Search ............ 435/69.4, 172.3, 252.31, 435/320.1; 536/27, 231.1, 231.4, 23.51; 935/47, 48, 74

[56] References Cited

PUBLICATIONS

Sigma Chemical Company Biochemicals, Organic Compounds for Research and Diagnostic Reagents, 1992, p. 1329.
Nakayama et al; J. Biotechnology 5: 171 (1987).
Vasantha et al; Gene 49: 23 (1986).
Stahl et al; J. Bacteriology 158: 411 (1984).

*Primary Examiner*—James Martinell
*Attorney, Agent, or Firm*—Hedman Gibson & Costigan

[57] ABSTRACT

A hybrid plasmid which is capable of inducing the expression and the secretion of human growth hormone (hGH) in its natural form and a method for the preparation of hGH which comprises the culture in a suitable environment of Bacillus subtilis cells transformed by the hybrid plasmid, are described.

The hGH thus obtained has the correct amino acid sequence and is particularly useful for treatment of man.

5 Claims, 3 Drawing Sheets

METHOD FOR THE PREPARATION OF HUMAN GROWTH HORMONE

This application is a continuation of application Ser. No. 07/233,162, filed Jul. 22, 1988, which is now abandoned.

DESCRIPTION

The present invention relates to the preparation of natural human growth hormone (hGH) by recombinant DNA techniques.

In particular, the present invention concerns a hybrid plasmid which is capable of inducing the expression and the secretion of natural human growth hormone from *Bacillus subtilis* (*B. subtilis*) and a method for its preparation which comprises the growing in a suitable culture environment of *B. subtilis* cells transformed by the hybrid plasmid.

hGH is a protein having 191 amino acids and a molecular weight of 22,000 daltons and is produced in the anterior lobe of the pituitary gland or adenohypophysis throughout the life of an individual but in greater quantities during the preadult period.

The growth hormone is synthesised in the form of the precursor and once processed is secreted from the cell.

Although its operating mechanism is not yet clear, it is known that hGH promotes skeletal growth, the retention of nitrogen and the synthesis of proteins and affects lipid and carbohydrate metabolism.

hGH is used for curing some forms of dwarfism which are linked to hormone deficiency and is also used in the treatment of obesity and in the cure of burns and wounds.

Up to a few years ago, the only available source of the hormone was represented by the hypophyses of cadavers from which it is extracted by a complex and expensive method.

Methods have recently been developed for the preparation of hGH by fermentation using host organisms transformed by recombinant DNA techniques.

In particular, patent no. GB 2055982 and patent no. EP 20147 describe a method for the production of growth hormone which comprises the growing of *Escherichia coli* (*E. coli*) cells transformed by a hybrid plasmid containing the structural sequence of the DNA which codes for mature hGH positioned downstream of a promotor and of a recognition site which are necessary for the transcription and translation processes and juxtaposed to the ATG triplet which codes for methionine which is necessary since it represents the starting signal for the translation of all the proteins.

However, with the use of these known methods, on the one hand the separation and purification of the synthesised hormone is difficult, and on the other hand hGH is produced which has an incorrect amino acid sequence.

In fact it has been found that the presence of methionine at the amine terminal of hGH alters the conformation of the molecule, affecting its activity and immunological characteristics.

Moreover, the use of *E. coli*, a bacterium which is pathogenic in man and is incapable of secreting the expression products into the outside environment makes the method itself quite onerous and, in particular, complicates the hGH separation and recovery stages.

Other methods have therefore been proposed in the art for the production of hGH, based essentially on the use of *Bacillus subtilis* (*B. subtilis*), a bacterium which is not pathogenic in man and which is able to secrete the proteins into the culture medium.

For this purpose the publication of A. Nakayama et al., 1987 (J. of Biotechnol. 5, 171-179) is cited, and relates to a method for the expression and secretion of human growth hormone from *B. subtilis* cells transformed by a hybrid plasmid obtained by the union of a cloning vector of *B. subtilis* with the sequence coding for natural hGH bound to the initial sequence of the prepropeptide of the neutral protease gene of *B. amyloliquefaciens* which codes for the secretion of the protein.

However, with this method the human growth hormone is secreted in the form of fused protein, that is, it is constituted by the mature hGH sequence and the amino acid sequence, resulting from the union of the region which codes for the prepropeptide and the structural gene of hGH.

As a result this method is not very attractive for application on a commercial scale.

A hybrid plasmid has now been constructed which enables the problems of the prior art to be overcome.

The object of the present invention is therefore a hybrid plasmid which can induce the expression and secretion of human growth hormone in its natural form.

Another object of the present invention is a method for the preparation of the natural human growth hormone by the fermentation of *Bacillus subtilis* cells transformed by the said hybrid plasmid.

A further object of the present invention is the use of the hormone thus obtained in the therapeutic and diagnostic fields.

Another object of the present invention is pharmaceutical compositions containing a therapeutically effective quantity of the hormone.

Other aims of the present invention will become clear from a reading of the description and of the examples which follow.

The hybrid plasmid according to the invention is obtained by the union of a cloning vector of *B. subtilis* with the gene which codes for mature hGH, fused at its 5′ terminal to the sequence which codes for the secretion signal of a serinic protease.

In particular, the plasmid is constructed by a method which comprises:

a) the digestion of a *B. subtilis* cloning vector with suitable restriction enzymes;

b) the digestion of the hybrid plasmid pSM209 with restriction enzymes FnuDII and HindIII and the isolation of the 530 bp fragment;

c) the synthesis of an artifical oligonucleotide which codes for the signal sequence responsible for the secretion of a serinic protease and for the 1-16 amino acid sequence of hGH;

d) the ligation of the DNA fragments obtained in stages a), b) and c) in the presence of T4 DNA ligase and finally, e) the isolation of the hybrid plasmid with the desired characteristics.

Suitable vectors for the purposes of the present invention may be selected from thoseknown in the art.

Preferably, the ATCC 67320 pSM 214 vector is used, which is characterised by good stability in *B. subtilis* and is capable of inducing efficient expression of the heterologous proteins. The ATCC is located in Rockville, Md., USA. This vector, produced by the method described in Italian application No. 19551 A/87, contains the functional origins of replication of pUB110 and pBR322 which enable the replication in *B. subtilis* and in *E. coli* of Km, Bla and Cat genes which code respectively for resistance to kanamycin, ampicillin and chloramphenicol, a strong artifical promotor which directs the transcription of a dicistronic messenger RNA (mRNA) including the Bla and Cat gene sequences and finally the to terminator of the lambda phage of *E. coli* situated downstream of the Cat gene.

The removal from the vector of the Bla gene with restriction enzymes EcoRI and HindIII and the subsequent introduction into the sites of a heterologous gene enables the construction of a hybrid plasmid in which the transcription of the gene is ensured, by the presence of the single promotor, with selection on chloramphenicol.

According to the present invention therefore the heterologous gene is that which codes for the mature hGH protein, fused at its 5' terminal to the DNA which codes for the signal sequence responsible for the secretion of the serinic protease. In particular, the protease is subtilisin, an extracellular proteolytic enzyme produced by *B. subtilis* (Millet J., 1970, J. Appl. Bacteriol. 33, 207-219; Markland F. S. et al 1971, The Enzymes, edited by Bayer P. D., Vol 3 561-608, Academic Press New York).

Subtilisin, synthesised by *B. subtilis* as a preproenzyme, contains at its N-terminal a signal sequence of 29 amino acids (leader peptide) which is responsible for activating the transportation of the protein through the membrane.

The signal sequence is removed by virtue of the activity of a specific endopeptidase which recognises the Ala-Gln-Ala ↓ amino acid sequence as a cutting site.

Accordingly, an oligonucleotide is synthesised which codes for the leader peptide of subtilisin for the construction of the hybrid plasmid according to the present invention.

Although the use of leader peptides is known in the art (Nucleic Acids Reserch. Vol: 9, (11), 2577 (1981); Gene 15, 43 (1981) for the preparation of hybrid plasmids for the secretion of heterologous proteins, it is not, however, possible to forecast the ability of these sequences to induce secretion when bound to heterologous genes.

In accordance with the present invention, an artificial oligonucleotide is constructed with replicates the sequences which code for the leader peptide of subtilisin from the methionine initiator up to the presumed cutting site for the Ala-Gln-Ala endopeptidase immediately followed by the sequence which codes for the aminoacids 1-16 of hGH.

The oligonucleotide synthesised according to one of the generally known techniques with the used automatic synthesiser, has the following sequence:

SUBTILISIN LEADER

Met Arg Ser Lys Lys Leu Trp Ile Ser Leu Leu Phe Ala Leu Thr Leu Ile Phe Thr Met Ala Phe Ser Asn Met Ser Ala Gln Ala | Phe Pro
GGAATTCTTATGAGAAGCAAAAATTGTGGATCAGCTTGTGTTTGCGTTAACGTTAATCTTTACGATGGCATTCAGCAACACATGTCTGCGCAGGCCTTCCCA
CCTTAAGAATACTCTTCGTTTTTAACACCTAGTCGAACAACAAACGCAATTGCAATTAGAAATGCTACCGTAAGTCGTTGTACAGACGCGTCCGGAAGGGT hGH →
↓ +1 +2

+3  +4  +5  +6  +7  +8  +9  +10 +11 +12 +13 +14 +15 +16
Thr Ile Pro Leu Ser Arg Leu Phe Asp Asn Ala Met Leu Arg
ACCATTCCCTTATCCAGGCTTTTGACAACGCTATGCTCCG
TGGTAAGGGAATAGGTCCGAAAAACTGTTGCGATACGAGGC    hGH

The removal of the 530 bp fragment which codes for the amino acids 17-191 of hGH from the plasmid pSM209 is then carried out as described in Italian patent application No. 20345 A/86.

In practice, this plasmid is treated in succession with FnuDII and HindIII restriction enzymes (BIOLABS) operating under the conditions recommended by the suppliers and separated by electrophoresis on polyacrylamide gel.

According to the present invention the ligation reaction between the EcoRI/HindIII 6500-base pair fragment of pSM214, the 530 base-pair FnuDII/HindIII fragment, and the artificial oligonucleotide is then carried out. The reaction is conducted in the presence of T4 DNA ligase enzyme with the fragments in a ratio of 1, 3, 3. Upon completion of the reaction, the entire mixture is used to transform B. subtilis cells made competent by Contente and Dubnau's method (Mol. Gen. Genet. 167-258 (1979)).

Various strains of B. subtilis may be used for this purpose.

In particular, the SMS 118 B. subtilis strain is used (leu, pyr Di, npr−, spr−) neutral protease minus and serinic protease minus.

The transformed cells are then cultured on VY medium (selective) with the addition of chloramphenicol.

It was possible, by operating in this manner to isolate from one of the positive clones thus obtained the hybrid plasmid pSM260 which upon electrophoretic and sequence analysis displayed the expected characteristics.

This plasmid was deposited as B. subtilis SMS 118 (pSM260) at the American Type Culture Center collection on 24/7/1987 as ATCC 67473.

According to the present invention and in order to check the ability of the hybrid plasmid to induce the expression and secretion of hGH in the natural form, B. subtilis SMS118 cells, transformed by pSM260 are grown in a suitable liquid medium in the presence of a source of carbon and of chloramphenicol as an inducer.

The B. subtilis SMS 118 (pSM260) cells are preferably grown in VY medium (Veal Infusion broth (DIFCO), Yeast Extract (DIFCO) in the presence of glucose at a temperature of approximately 37 degrees centigrade.

The proteins present in the cell extract and in the supernatant liquor of the culture are then analysed by electrophoresis on polyacrylamide gel (Laemmli, 1970, Nature, 277, 680) and the hGH was displayed both by dyeing with Coomassie Blue ("Gel Electrophoresis of proteins: a practical approach", edited by B. D. Hames and D. Rickwood, published by IRL Press Limited) and by transfer onto nitrocellulose filters and subsequent treatment of the filters with anti-hGH antibodies.

The results obtained show the presence in the supernatant liquor of a protein which comigrates with the hGH standard (Calbiochem) and which gives a positive immunoreaction with the anti-hGH antibodies.

A protein is found in the cell lysate, however, which has a molecular weight a little greater than that of mature hGH, and is probably derived from a partial digestion of the hGH precursor (subtilis leader peptide +mature hGH).

The ratio between the quantity of precursor and of hGH secreted, determined by estimating the strength of the two proteins on SDS-PAGE, shows a secretion activity of between 80 and 90%.

The aminoterminal sequence of the hGH thus secreted, determined by the method of Edman, P. et al, 1967 (J. Biochem. 80-91) with the use of the automatic protein sequencer model B90A (Beckman), shows the sequence expected for the natural hormone, thus confirming the correct processing of the precursor synthesised from the B. subtilis cells transformed by the plasmid according to the present invention.

Figure 1:
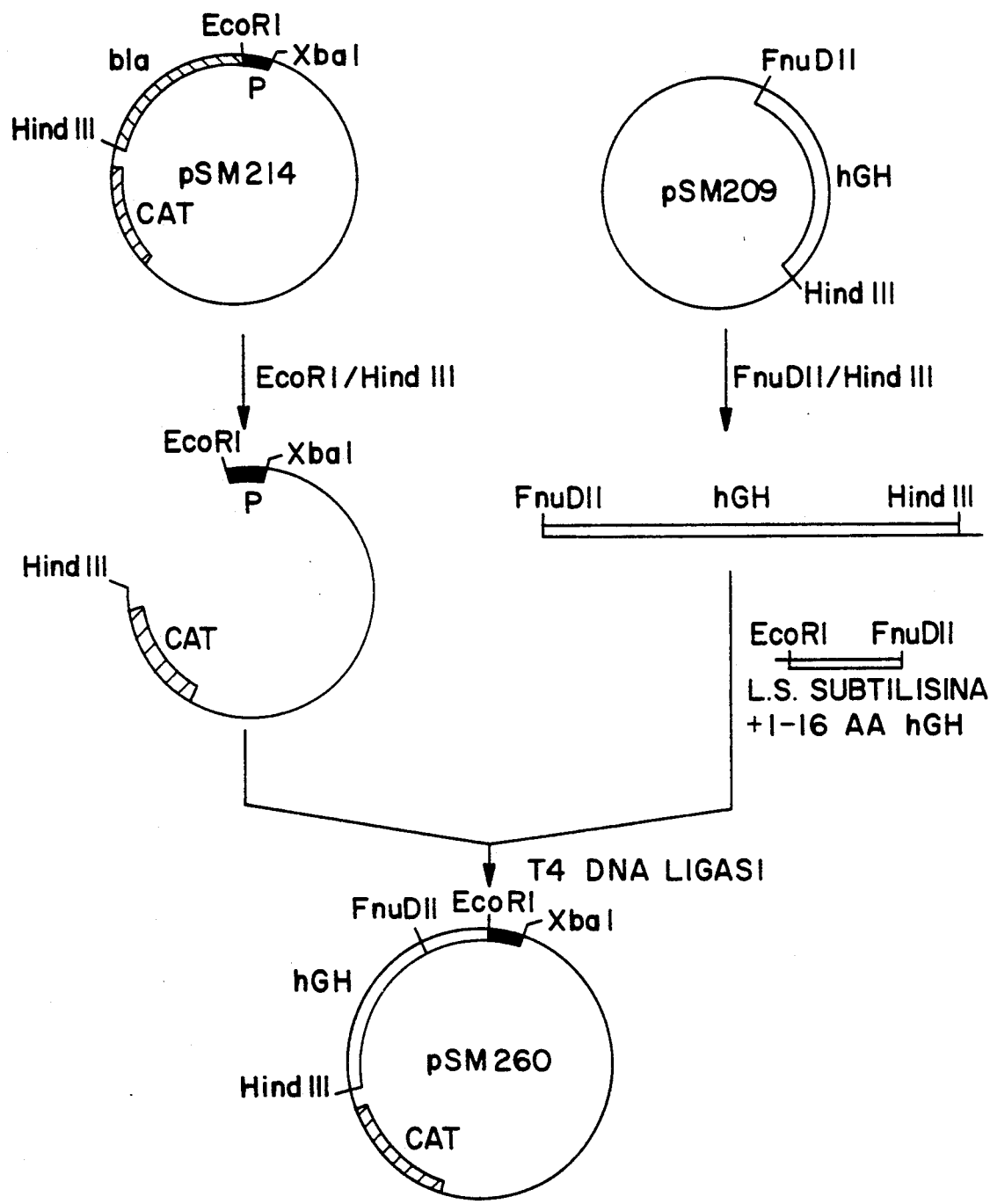
FIG. 1: a schematic representation of the construction of the plasmid pSM260.

A: SMS 118 (pSM214) total proteins
B: SMS118 (pSM214) extracellular protein fraction
C: SMS118 (pSM260) total proteins
D: SMS118 (pSM260) extracellular protein fraction
E: met-hGH The following examples are illustrative of the invention and are not limiting.

EXAMPLE 1

Construction of the hybrid plasmid pSM260.

a) Construction of the hGH gene and its insertion into the plasmid pSM214

FIG. 1

2 μg of the plasmid ATCC 67320 pSM214 were digested in 50 μl of a buffer containing 50 mM Tris-HCl (pH 7.5), 6 mM MgCl$_2$, and 50 mM NaCl with 2 Units (U) of EcoRI and HindIII restriction enzymes (BRL) at 37 degrees centigrade for 1 hour.

The enzyme reaction was then stopped by extraction of the reaction mixture with phenol-chloroform (1:1, V/V) and chloroform isoamyl (24:1, V/V) and the DNA precipitated with ethanol at −20 degrees centigrade and separated by centrifuging in an Eppendorf centrifuge at 12000 rpm for 20 minutes. The plasmid DNA was then resuspended in 10 μl of TE buffer (50 mM of Tris-HCl, 1 mM EDTA pH 8.0) loaded onto 0.6% agarose gel and run at 100volts for 1 hour.

The band corresponding to the 6500 bp DNA fragment was the electroeluted at 125 V for 90 minutes.

The 530 bp fragment containing the sequence which codes for hGH 17-191 was simultaneously isolated from hybrid plasmid pSM209 (described in Italian patent application No. 20345 A/86 which has been deposited at the Centraalbureau Voor Schimmelculture, Oosterstraat 1, Postbus 273, NL-3740 AG baarn, Netherlands on Dec. 22, 1988 under Deposit No. CBS 753.88.

For this purpose, 50 μg of pSM209 were digested in 200 μl of a reaction mixture containing 6 mM Tris-HCl (pH 7.4), 6 mM NaCl, 6 mM MgC$_2$, and 6 mM of mercaptoethanol with 50 U of FnuDII (Biolabs), which cuts the DNA between aminoacids 16 and 17, at 37 degrees centigrade for 1 hour.

After the enzyme had been deactivated at 70 degrees centigrade for 10 minutes, the solution was brought to a concentration of 50 mM Tris-HCl (pH 8.0), 10 mM MgCl$_2$, and 50 mM NaCl, incubated at 37 degrees centigrade for 1 hour in 15 presence of 50 U of HindIII (Boehringer): After the enzyme had been de-activated, the DNA was separated on 6% acrylamide gel at 130 volts for 3 hours.

The band of approximately 530 base pairs was then eluted as described by Maxam and Gilbert (Methods in Enzymology Vol. 65 p 499-560 1980).

Finally, the DNA fragment shown below was synthesised with the use of a System One DNA Synthesizer (Beckman):

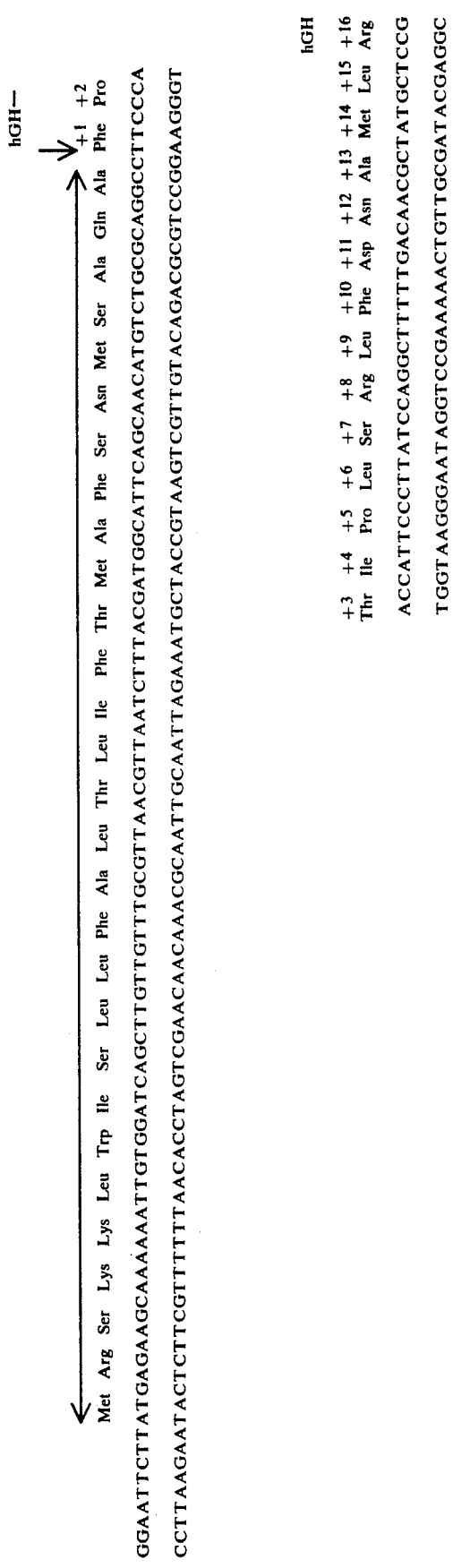

This fragment codes for the sequence of 29 amino acids of the peptide leader of subtilisin and for the amino acids 1-16 of hGH. 1 μg of this artificial fragment was then phosphorylated in 20 μl of a buffer containing 66 mM Tris-HCl pH 7.6, 1 mM Spermidine, 10 mM MgCl$_2$, 15 mM DTT, 0.1 mM EDTA and 2 U T4 Kinase (Bioloabs) at 37 degrees centigrade for 1 hour.

The enzyme was then deactivated at 65 degrees centrigrade for 10 minutes. 400 ng of the 530 bp FnuDII-HindIII fragment, 100 ng of the artificial fragment phosphorylated as described above and 1.5 μg of the 6500 bp EcoRI-HindIII fragment of pSM214 were mixed in 10 μl of a buffer containing 66 mM Tris-HCl (pH 7.6), 1 mM ATP, 10 mM MgCl$_2$, and 10 mM dithiothreitol (DTT) and ligated in the presence of 2 U T4 DNA ligase at 14 degrees centigrade for 18 hours.

The ligase mixture was then used to transform SMS118 B. subtilis cells made competent by Contente and Dubnau's method (Mol. Gen. Genet. 167, 251-258 (1979)).

The cells thus transformed were then selected on TBAB plates (Tryptose Blood Agar Base) containing 5 μg/ml of chloramphenicol (Cm) and grown at 37 degrees centigrade for 18 hours.

Figure 2:
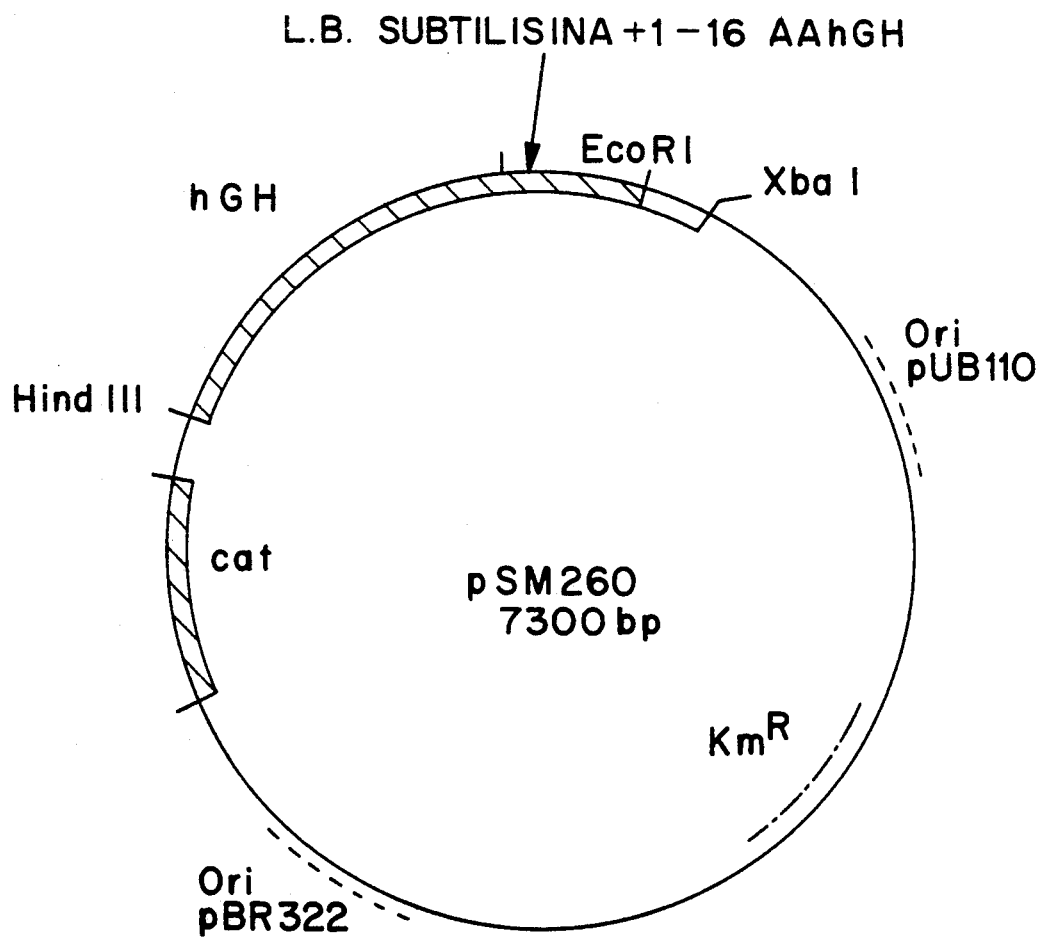
FIG. 2: shows the restriction map of the plasmid pSM260.

The expected hybrid plasmid (FIG. 2) known as pSM260, was isolated from one of the positive clones.

EXAMPLE 2

Expression and secretion of hGH in *Bacillus subtilis* SMS 118

*B. subtilis* SMS118 cells transformed by the hybrid plasmid pSM260 (*B. subtilis* SM118 (pSM260) were grown in 10 ml of VY medium (Veal Infusion Broth (DIFCO) 25 g/l yeast extract (DIFCO) 5 g/l) with the addition of 5 μg/ml of chloramphenicol and 3% of glucose, at 37 degrees centigrade for 18 hours.

1 ml of the culture was then centrifuged (10 minutes, 10,000 rpm) in an Eppendorf centrifuge, the cells washed twice with 1 ml of 30 mM Tris-HCl (pH 7.5), 50 mM NaCl buffer, centrifuged again, resuspended in 100 μl of SET buffer (20% sucrose, 50 mM Tris-HCl ph 7.6, 50 mM EDTA) and lysed by the addition of 20 μl of an aqueous solution containing 50 mg/ml of lysozyme (SIGMA) at 37 degrees centigrade for 5 minutes. To this mixture were then added 130 μl of buffer A (125 mM Tris-HCl pH 6.9, 3% SDS, 3% beta-mercaptoethanol and 20% glycerol) and the resulting solution was incubated at 90 degrees centigrade for 5 minutes.

Simultaneously, the proteins contained in the supernatant liquor of *B. subtilis* SMS118 (pSM260) were precipitated at 4 degrees centigrade over 60 minutes and added to 0.8 ml of culture medium, 0.3 ml of 20% TCA (Trichloroacetic acid).

The precipitate wash washed with acetone 2-3 times and after centrifuging, resuspended in 30 μl of SET buffer and after the addition of 50 μl of buffer A, was incubated at 90 degrees centigrade for 5 minutes.

25 μl of cell lysate and 20 μl of the protein solution of the supernatant liquor were loaded onto 12.5% SDS-acrylamide gel (Laemmli (1970)) Nature, 277, 680) and after electrophoresis at 25 mA for 3 hours, the proteins were made evident both with Coomassie Blue ("Gel Electrophoresis of proteins: a practical approach" edited by B. D. Hames and D. Rickwood IRL Press Limited) and by means of transfer onto nitrocellulose filters (Shleiher & Shull 45 μm pore size-Towbin) and treatment of the filters with rabbit anti-hGH antibodies (Miles) and goat anti-rabbit-IgG antibodies combined with peroxidase (Miles).

After dyeing with Coomassie Blue, the presence of a protein which comigrates with the hGH standard (Calbiochem) in the supernatant liquor of the growing culture of the *B. subtilis* SMS118 (pSM 260) strain, is made evident.

Figure 3:
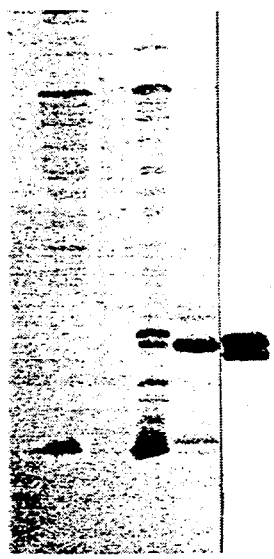
FIG. 3: A WESTERN-BLOT of the total proteins extracted from B. subtilis cells and of the fraction secreted into the culture medium.

This protein gives a position immunoreaction with the anti-hGH antibodies (FIG. 3).

Analysis of the proteins obtained after cell lysis showed the presence of a residual protein which is reactive against the anti-hGH antibodies and whose molecular weight could correspond to the partially processed subtilisin LS+hGH precursor.

The ratio between the quantities of hGH precursor and the hGH protein secreted, determined by estimating the strength of the two positive bands to exposure to antibodies (immunoblot), indicated a secretion of >80% of the hormone expressed by *B. subtilis* SMS118(pSM260).

EXAMPLE 3

Purification of secreted hGH

A *B. subtilis* SMS118 (pSM260) culture, glycerinated and preserved at −80 degrees centigrade was used to obtain individual colonies on L agar plates contained 5 μg/ml of chloramphenicol.

A Cm resistant colony was then used to inoculate 1 l of VY medium supplemented with 5 μg/ml of chloramphenicol and 3% glucose.

The culture was grown with gentle agitation at 37 degrees centigrade for 18 hours.

The supernatant liquor of the growth was then separated from the cells by centrifuging (10 minutes, 7000 rpm) in a Sorvall rotor.

The proteins were then precipitated by the addition to the supernatant liquor at 4 degrees centigrade of 0.39 g/ml of ammonium sulphate (MERCK) (60% saturation) and, after 24 hours, the precipitate was collected by centrifuging at 5000 rpm for 10 minutes.

The precipitate was then dissolved in 35 ml of 20mM Tris-HCl solution pH 8.0 and then dialysed extensively against the same buffer. A 20 cm×2.6 cm column (total volume 106 ml) of DEAE CL-68 Sepharose (Pharmacia) equilibrated with 20 mM Tris-HCl, pH 8.0 (flow rate 70 ml/hour) was loaded with the protein solution.

After the column had been washed with three volumes of the equilibrating buffer, the proteins were eluted with 20 mM Tris-HCl (pH8.0), 0.1 M NaCl buffer.

The fractions containing hGH were collected and the hormone was concentrated by the addition of ammonium sulphate as described above.

Upon electrophoretic analysis (SDS-PAGE), the hGH was more than 95% homogeneous and the yield, calculated as the ratio between the hGH loaded and the hGH eluted, was 80%.

Further purification may be effected by hydrophobic and affinity chromatography and gel filtration.

The hGH thus purified was then used to determine the aminoterminal amino acid sequence by automatic degradation by Edman's method using a Beckman 890 M model automatic sequencer.

The results obtained show a protein with an aminoterminal sequence identical to that expected for hGH.

We claim:

1. Hybrid plasmid pSM260 capable of inducing the expression and secretion of human growth hormone which is identical to natural human growth hormone in *Bacillus subtilis* having the deposit accession number ATCC 67473.

2. The hybrid plasmid according to claim 1, obtained by a method which comprises:
a) digesting vector pSM214 (ATCC 67320) with restriction enzymes EcoRi and HindIII and separating the 6500 base pair EcorI/HindIII fragment;
b) digesting plasmid pSM209 with restriction enzymes FnudII and HindIII and separating the 530 base pair FnuDII/HindIII fragment coding the 17–191 amino acid sequence of human growth hormone;
c) synthesizing an oligonucleotide having the DNA sequence which codes the leader peptide of subtilisin and the 1–16 amino acid sequence of human growth hormone;
d) ligating the fragments obtained in steps a), b) and c) with T4 DNA ligase; and
e) recovering the resulting plasmid.

3. A *Bacillus subtilis* transformed by the hybrid plasmid of claim 1.

4. The microorganism according to claim 3, wherein the *Bacillus subtilis* is strain SM118 minus neutral protease and serinic protease.

5. A process for producing human growth hormone which is identical to natural human growth hormone, culturing *Bacillus subtilis* SMA 118 (pSM260) ATCC 67473 in a aqueous nutrient medium and therafter recovering said process comprising secreted human growth hormone which is identical to natural human growth hormone therefrom.

* * * * *